United States Patent
Fei et al.

(10) Patent No.: US 6,485,716 B1
(45) Date of Patent: Nov. 26, 2002

(54) HIGH EFFICACY LIQUID GEL PRODUCT

(75) Inventors: Lin Fei, Kendall Park, NJ (US); Suman Chopra, Dayton, NJ (US); Eric Guenin, Pennington, NJ (US); Peter Hilliard, Jr., Far Hills, NJ (US); Jairajh Mattai, Piscataway, NJ (US); Neeta Patel, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/971,876

(22) Filed: Oct. 5, 2001

(51) Int. Cl.⁷ .............................. A61K 7/32; A61K 7/00
(52) U.S. Cl. .......................... 424/65; 424/400; 424/401
(58) Field of Search ............................ 424/65, 400, 401

(56) References Cited

U.S. PATENT DOCUMENTS

| | | |
|---|---|---|
| 4,673,570 A | 6/1987 | Soldati |
| 4,900,542 A | 2/1990 | Parrotta, Jr. et al. |
| 4,937,069 A | 6/1990 | Shin |
| 4,944,938 A | 7/1990 | Potini |
| 5,069,897 A | 12/1991 | Orr |
| 5,102,656 A | 4/1992 | Kasat |
| 5,587,153 A | 12/1996 | Angelone, Jr. et al. |
| 5,863,525 A | 1/1999 | Angelone, Jr. et al. |
| 6,007,799 A | 12/1999 | Lee et al. |

OTHER PUBLICATIONS

U.S. patent application Ser. No. 09/693,231, Chopra et al., Oct. 20, 2000.

U.S. patent application Ser. No. 09/693,229, Chopra et al., Oct. 20, 2000.

U.S. patent application Ser. No. 09/693,248, Chopra et al., Oct. 20, 2000.

*Primary Examiner*—Shelley A. Dodson
(74) *Attorney, Agent, or Firm*—Rosemary M. Miano

(57) ABSTRACT

The invention is a clear, elastomer-free, gel composition comprising: (a) 0.1–25 weight % of an antiperspirant active having a low metal to chloride ratio in the range of 0.9–1.3:1; (b) 9–23.95 weight % of one or more volatile silicones having a flash point of 100 degrees C or less; (c) 0.05–0.5 weight % of a silicone surfactant having an HLB value $\leq 8$; (d) 30–70 weight % water; (e) 0–50 weight % selected water soluble organic solvents; and (f) 0–10 weight % of an emollient; wherein the composition is a liquid gel having a viscosity in the range of 5–50,000 centipoise and a ratio of oil phase to water phase in the range of 10:90 to 24:76.

19 Claims, No Drawings

HIGH EFFICACY LIQUID GEL PRODUCT

FIELD OF THE INVENTION

The present invention is directed to a high efficacy gel composition which is a low viscosity liquid emulsion, is elastomer-free, and which comprises an antiperspirant active (preferably with a lower metal to chloride ratio) and a reduced amount of surfactant. Preferably the gel is formulated as a clear product. The product comprises antiperspirant active materials in amounts sufficient to combat body malodor either as a deodorant or as an antiperspirant when applied to the axillary regions of the body.

The present invention is particularly directed to elastomer-free cosmetic gel compositions, including antiperspirant and deodorant gel compositions, that have reduced whitening and tack, and reduced skin irritation, and which can include increased amounts of the cosmetically active ingredient (for example, increased amounts of antiperspirant active ingredient), and yet which can be effective with low levels of active as well.

BACKGROUND OF THE INVENTION

Antiperspirant products are well known in the art. Antiperspirants have appeared in the marketplace in varied dosage forms, such as sticks, soft solids, soft gels, roll-on, aerosols and creams. Generally, these dosage forms include a solution of the active ingredient in a suitable solvent, a suspension of the active ingredient in a non-solvent, or a multiphasic dispersion or emulsion in which a solution of the active ingredient is dispersed in some continuous phase or in which the solubilized active ingredient constitutes a continuous phase.

Of the above-referred-to dosage forms, the stick form is an example of a solid form, and the soft solid and soft gel are thickened forms which may or may not be solid (for example, under some circumstances, gels can flow). The stick form can be distinguished from a soft solid or soft gel in that, in a stick, the formulated product can retain its shape for extended time periods outside the package, the product not losing its shape significantly (allowing for some shrinkage due to solvent evaporation). Adjustment of amounts of gelling or thickening agents can be used in order to form a soft gel or stick.

Soft gels or soft solids can be suitably packaged in containers which have the appearance of a stick, but which dispense through apertures (for example, slots or pores) on the top surface of the package. The soft solid products have also been called soft sticks or "smooth-ons", and hereinafter are generically called "soft solids". Reference is made to U.S. Pat. No. 5,102,656 to Kasat, U.S. Pat. No. 5,069,897 to Orr, and U.S. Pat. No. 4,937,069 to Shin, each of which discloses such soft solids, including physical characteristics thereof such as viscosity and hardness. The contents of each of these three U.S. Patents are incorporated herein by reference in their entirety.

Recently, there has been significant activity in developing clear and translucent antiperspirant sticks and soft gels, particularly to provide sticks and soft gels having increased efficacy (for example, by providing increased amounts of the antiperspirant active in the sticks and soft gels), improved cosmetic characteristics (including reduced whitening, reduced residue and reduced tack), and reduced skin irritation potential (e.g., providing a product that is "mild").

U.S. Pat. No. 4,944,938 to Potini discloses clear, non-alcoholic, quick drying, antiperspirant and deodorant gels, which are stable both at room temperatures and at higher temperatures, are non-stinging and leave no white residue on the skin, the gel not including gelling agents, waxes, clays, or monohydric alcohols having 2–8 carbon atoms. The gels use 3–5 carbon atom trihydric alcohols as coupling agents, these alcohols acting as solublizers in the system and keeping the system stable and clear. The gels can include an aluminum active salt; a volatile water-insoluble emollient, such as isostearyl benzoate: a soluble emollient such as cetyl ether; solubilizers such as propylene glycol and glycerin; volatile siloxanes; and water.

Some cellulosic materials, such as hydroxypropylcellulose, among others, are compatible with polyvalent metal salts and have been used in the manufacture of clear lotions. These cellulosic materials, however, must be prepared with a high percentage of water or alcohol in order to insure solubilization of the active ingredient. The resulting formulations, in addition to a high irritation potential, are tacky and putties, and low in efficacy, when alcohol-based; and exhibit tackiness and along drying time when water-based.

Clear or translucent antiperspirant soft gels (which have been dispensed from containers having the appearance of stick) have recently been marketed, consisting of viscous, high-internal-phase emulsions. These soft gels exhibit some advantages over the aforementioned sticks, particularly acetal-based clear sticks, in that the selection of formulation ingredients is less restricted (for example, water can be used), and often tack can be reduced significantly. Concerning these emulsions, note U.S. Pat. No. 4,673,570 to Soldati and U.S. Pat. No. 4,900,542 to Parrotta, et al. These two U.S. patents disclose clear gelled antiperspirant compositions free of waxes and conventional gelling agents, containing a volatile silicone fluid, a silicone emulsifier, a destabilizing auxiliary emulsifier, water, non-volatile emollient, a coupling agent, an active antiperspirant component and ancillary agents such as perfume, coloring agents, etc. The silicone emulsifiers a cyclomethicone-dimethicone copolyol silicone fluid marketed by Dow Corning Corporation under the trademark DOW CORNING 3225C formulation. The contents of these two U.S. patents are incorporated herein by reference in their entirety.

Also to be noted is PCT (International application) Publication No. WO 92105767. This patent document discloses a clear gel-type cosmetic product having a viscosity of at least about 50,000 cps at 21 degrees C. and a refractive index of 1.3975–1.4025 at 21 degrees C., and having an optical clarity better than 50 NTU (Nephelometric Turbidity Units) at 21 degrees C., the product being an emulsion with a water phase having an active ingredient incorporated therein and with an oil phase. The refractive indices (measured at 5893 Angstroms) of the water and oil phases match to within 0.0004. The oil phase includes an emulsifier which when properly mixed with the water phase component yields a water-in-oil emulsion, and the water phase includes one or a combination of various polar species such as water, propylene glycol, sorbitol and ethanol. The water phase includes the deodorant and/or antiperspirant active ingredient. The contents of this PCT (International application) Publication No. 92/05767 are incorporated herein by reference in their entirety.

U.S. Pat. No. 6,007,799 describes clear cosmetic gels that are water-in-oil emulsions and which comprise at least one coupling agent, silicone fluids and an alkoxylated, alkyl substituted silicone surface active agent.

U.S. Pat. Nos. 5,587,153 and 5,863,525 issued to Gillette also describe gel products that contain silicone.

U.S. Pat. No. 6,007,799 assigned to the same owner as this case describes a clear cosmetic gel made as a water-in-oil emulsion.

While various cosmetic gel compositions, including antiperspirant and deodorant compositions, that are clear, are known, it is still desired to provide a cosmetic liquid gel composition (e.g., clear antiperspirant and/or deodorant gel composition) which has improved efficacy in comparison to other products, especially other commercially available gel products. It is a further object of the invention to provide products which have reduced whitening, low tack, and reduced skin irritation potential relative to commercially available products. It is yet another object of the invention to provide gel antiperspirant/deodorant products which provide improved efficacy even with low levels (for example, 5 weight % based on the entire composition) of antiperspirant active, use reduced amounts of volatile silicones and copolyols, have improved efficacy and low viscosity.

SUMMARY OF THE INVENTION

The invention is a high efficacy gel composition (preferably clear) which is a low viscosity (5–50,000 centipoise) liquid emulsion, is elastomer-free, and which comprises an antiperspirant active (preferably with a lower metal to chloride ratio) and a reduced amount of surfactant. This gel composition comprises:

(a) 0.1–25 weight % (more particularly 5–20 weight %) of an antiperspirant active (preferably one having a low metal to chloride ratio in the range of 0.9–1.3:1 (more particularly in the range of 0.9–1.05:1) (metal being one or both of aluminum and zirconium);

(b) 9–23.95 weight % (more particularly 9–20 weight %) of one or more volatile silicones having a flash point of 100 degrees C or less;

(c) 0.05–0.5 weight % (for example, 0.1–0.2%, particularly 0.1–0.15% of a silicone surfactant having an HLB value (hydrophilic lipophilic balance)$\leq 8$);

(d) 30–70 weight % water (particularly 45–65% and, more particularly, 50–60%);

(e) 0–50 weight % of a water soluble organic solvent (for example, ethanol, glycerol formal (a mixture of 5-hydroxy-1,3-dioxane and 4-hydroxymethyl-1,3-dioxolane, also known as methylidinoglycerol), propylene glycol, dipropylene glycol, or tripropylene glycol; and (f) 0–10 weight % of an emollient (particularly 0–5%) (for example, a member of the group consisting of hydrogenated polyisobutene (Polyiso 250), C12–15 alkyl benzoate (FINSOLV TN), and PPG-3 myristyl ether); wherein the composition is an emulsion and the ratio of oil phase to water phase is in the range of 10:90 to 24:76.

According to a first aspect of the present invention, various of the foregoing objects are achieved through a liquid cosmetic gel composition which is an emulsion having (1) an aqueous phase containing water (or water and a water soluble organic solvent as defined above) and at least one antiperspirant active; and (2) an oil phase containing a volatile organic or silicone material, and the composition further including (3) a suitable surfactant in a low amount such as an alkoxylated, alkyl substituted siloxane surface active agent in an amount of 0.05–1.0 weight % as described above. Preferably, the refractive index of the composition before the addition of any fragrance is in a range of from about 1.3950 to about 1.4150; especially from about 1.4000 to about 1.4050, and most preferably the refractive index of the composition is in a range of from about 1.4000 to about 1.4025. Refractive index measurements were made at a temperature of about 20–25 degrees C using a Bausch and Lomb Abbe 3L Refractometer.

When a clear formulation is desired, the water content should be, for example, in the range of about 50–60 weight %.

Addition of fragrance to the gel composition according to the present invention may increase the refractive index of the finished product. The refractive index referred to previously (e.g., a broadest range of 1.3950 to 1.4150) is the refractive index prior to incorporating fragrance in the composition.

By providing a composition having the specified refractive index, a composition containing more of the cosmetically active ingredients (in particular, more of the antiperspirant active ingredient such as an antiperspirant active salt, where the composition is a clear antiperspirant gel composition) can be achieved.

Moreover, this composition having the specified refractive index can also include high refractive index components, in either the oil phase or the aqueous phase, or additional amounts of high refractive index components, that provide advantageous cosmetic or other aesthetic effects. That is, conventional clear compositions have a relatively low refractive index. These relatively low refractive indices of conventional clear compositions of the water-in-oil emulsion type are due at least in part to the relatively low refractive indices of various conventionally used silicone fluids (e.g., around 1.3995), incorporated in the oil phase of these conventional compositions. This limits materials (and amounts) that can be included in the conventional composition such that the emulsion as a whole has the required relatively low refractive index. This limitation can be avoided according to the present invention, providing an increased degree of freedom in the choice of materials that can be incorporated in both the aqueous and oil phases of the composition of the present invention. For example, emollients having a higher refractive index can be incorporated in the oil phase and in the water phase, especially in the oil phase, of compositions according to the present invention, having the relatively high refractive index. Since antiperspirant active materials generally have high refractive indices, these can be incorporated in larger amounts in compositions of the present invention. Moreover, materials having a high refractive index that can reduce tack and whitening of the composition can be incorporated in the oil phase of the composition of the present invention.

Desirably, the composition according to the present invention has refractive index matching between (1) the aqueous phase and (2) the oil phase. In particular and preferably according to the present invention, a difference between the refractive index of (1) the aqueous phase, and (2) the oil phase and alkoxylated, alkyl substituted siloxane surface active agent, is less than 0.0005.

Composition according to the present invention can be clear. For example, illustratively, the composition according to the present invention has an optical clarity less than approximately 50 NTU (Nephelometric Turbidity Units) at room temperature (20°–25° C.), preferably having a turbidity measurement of less than approximately 30 NTU, more preferably less than approximately 20 NTU. Turbidity measurements as discussed in the foregoing and discussed hereinafter, were made with an Orbeco-Hellige #965 Direct-Reading Turbidimeter.

The cosmetic gel composition of the present invention includes an antiperspirant active agent in an amount sufficient to have a deodorizing effect and/or in an amount sufficient to reduce the flow of perspiration when the composition is applied to a human. Such antiperspirants include those selected from the group consisting of any of the known antiperspirant active materials. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrides, or aluminum-stannous chlorohydrates, can be incorporated as an antiperspirant active ingredient in antiperspirant compositions according to the present invention.

Particular types of antiperspirant actives include aluminum zirconium trichlorohydrex and aluminum zirconium tetrachlorohydrex either with or without glycine. A particular antiperspirant active is aluminum trichlorohydrex gly such as REZAL 36G (from Reheis Inc., Berldey Heights, N.J.) and WESTCHLOR 35BX3 (from Westwood Chemicals, Middletown, N.Y.).

Antiperspirant actives can be incorporated into compositions according to the present invention in amounts in the range of 0.1–25% of the final composition, but the amount used will depend on the formulation of the composition. For example, at amounts in the lower end of the broader range (for example, 0.1–9% on an actives basis), a deodorant effect may be observed. At lower levels the antiperspirant active material will not substantially reduce the flow of perspiration, but will reduce malodor, for example, by acting as an antimicrobial material. At amounts of 9–25% (on an actives basis) such as 15–25%, by weight, of the total weight of the composition, an antiperspirant effect may be observed.

Particularly preferred are antiperspirant actives having the specific low metal to chloride ratio specified above and those described in co-pending cases assigned to the same owner as this application (U.S. patent application Ser. No. 09/693,231 filed on Oct. 20, 2000 and U.S. patent application Ser. No. 09/693,248 filed on Oct. 20, 2000. Another case of interest is U.S. Ser. No. 09/693,229 filed on Oct. 20, 2000.

Actives of special interest because they form low RI solutions include: Westchlor Zr 35BX3 (30–35% actives in water) from Westwood Chemical Company, Middletown, NY; Rezal 36G (46% in water) from Reheis Inc., Berkeley Heights, N.J.; Summit AZG-368 (28–32% in water) from Summit Research Labs, Huguenot, N.Y.; Reach 301 (39% in water) from Reheis Inc.; and aluminum chloride (28% in water) which may be obtained from several sources. In general, the metal:chloride mole ratio is approximately 1.4:1 for such salts.

In one particular type of salt of interest, an aluminum zirconium tetra salt with glycine is used wherein aluminum zirconium tetrachlorohydrex glycine salt having a metal to chloride ratio in the range of 0.9–1.2:1 (especially in the range of 0.9–1.1:1 and, more particularly in the range of 0.9–1.0:1); and a glycine:zirconium mole ratio greater than 1.3:1, particularly greater than 1.4:1. This type of salt may be made in a variety of ways as described in a co-pending case U.S. Ser. No. 09/693,231 referenced above.

Method A: An aluminum chlorohydrate (ACH) solution of ACH salt in water of suitable concentration is mixed with an aqueous solution of zirconyl chloride ($ZrOCl_2$) of suitable concentration and powdered glycine. The mixture is stirred at room temperature to obtain the salt.

Method B: A suitable commercially available aluminum zirconium tetrachlorohydrex glycine salt is obtained and mixed with a sufficient amount of an aqueous aluminum chloride ($AlCl_3$) solution and powdered glycine. The mixture is stirred at room temperature to obtain the salt. When Method B is used, a suitable salt to use as a starting material includes various types of tetra salts such as aluminum zirconium tetrachlorohydrex gly, aluminum zirconium tetrachlorohydrex gly propylene glycol complex, aluminum zirconium tetrachlorohydrex gly dipropylene glycol complex, and mixtures of any of the foregoing. These salts may be referred to hereinafter as experimental salts or carry an "exp" suffix in their designation. It is preferred that the experimental salt be used in the form of a 28–50% water solution when added to form the compositions of the invention.

Suitable silicone surfactants include silicone polyglucosides (for example, octyl dimethicone ethoxy glucoside) and silicone copolyols having an HLB value (hydrophilic lipophilic balance)$\leq 8$. The HLB value may be measured in a variety of ways such as described in conventional references or found listed in tables of data recording such values. It is intended that any type of HLB measurement technique may be used.

A silicone copolyol (especially dimethicone copolyol) may be used in an amount of 0.05–0.5 weight % (actives basis), particularly 0.1–0.2% and, more particularly, 0.1–0.15%.

In general, silicone copolyols useful in the present invention include copolyols of the following Formulae I and II. Formula I materials may be represented by:

$(R^{10})_3$—SiO—$[(R^{11})_2$—SiO$]_x$—$[Si(R^{12})(R^b$—O—$(C_2H_4O)_p$—$(C_3H_6O)_s$—$R^c)O]_y$—Si—$(R^{13})_3$ 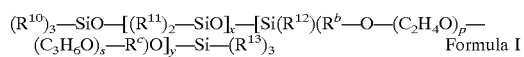 Formula I wherein each of $R^{10}$, $R^{11}$, $R^{12}$ and $R^{13}$ may be the same or different and each is selected from the group consisting of C1–C6 alkyl; $R^b$ is the radical —$C_mH_{2m}$—; $R^c$ is a terminating radical which can be hydrogen, an alkyl group of one to six carbon atoms, an ester group such as acyl, or an aryl group such as phenyl; m has a value of two to eight; p and s have values such that the oxyalkylene segment —$(C_2H_4O)_p$ —$(C_3H_6O)_s$— has a molecular weight in the range of 200 to 5,000; the segment preferably having fifty to one hundred mole percent of oxyethylene units —$(C_2H_4O)_p$— and one to fifty mole percent of oxypropylene units —$(C_3H_6O)_s$—; x has a value of 8 to 400; and y has a value of 2 to 40. Preferably each of $R^{10}$, $R^{11}$, $R^{12}$ and $R^{13}$ is a methyl group; $R^c$ is H; m is preferably three or four whereby the group $R^b$ is most preferably the radical —$(CH_2)_3$—; and the values of p and s are such as to provide a molecular weight of the oxyalkylene segment —$(C_2H_4O)_p$—$(C_3H_6O)_s$— of between about 1,000 to 3,000. Most preferably p and s should each have a value of about 18 to 28.

A second siloxane polyether (copolyol) has the Formula II:

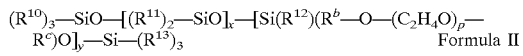

$$(R^{10})_3-SiO-[(R^{11})_2-SiO]_x-[Si(R^{12})(R^b-O-(C_2H_4O)_p-R^c)O]_y-Si-(R^{13})_3 \qquad \text{Formula II}$$

wherein p has a value of 6 to 16; x has a value of 6 to 100; and y has a value of 1 to 20 and the other moieties have the same definition as defined in Formula I.

It should be understood that in both Formulas I and II shown above, that the siloxane-oxyalkylene copolymers of the present invention may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Thus, one or more of the $R^{10}$, $R^{11}$, $R^{12}$ and $R^{13}$ substituents which are attached to the two terminal silicon atoms at the end of the siloxane chain can be substituted with the segment $-R^b-O-(C_2H_4O)_p-(C_3H_6O)_s-R^c$ or with the segment $-R^b-O-(C_2H_4O)_p-R^c$. In some instances, it may be desirable to provide the segment $-R^b-O-(C_2H_4O)_p-(C_3H_6O)_s-R^c$ or the segment $-R^b-O-(C_2H_4O)_p-R^c$ at locations which are in the siloxane chain as well as at locations at one or both of the siloxane chain ends.

Particular examples of suitable dimethicone copolyols are available either commercially or experimentally from a variety of suppliers including Dow Corning Corporation, Midland, Mich.; General Electric Company, Waterford, N.Y.; Witco Corp., Greenwich, Conn.; and Goldschmidt Chemical Corporation, Hopewell, Va. Examples of specific products include DOW CORNING® 5225C from Dow Corning which is a 10% dimethicone copolyol in cyclomethicone; DOW CORNING® 2-5185C which is a 45–49% dimethicone copolyol in cyclomethicone; SILWET L-7622 from Witco; ABIL EM97 from Goldschmidt which is a 85% dimethicone copolyol in D5 cyclomethicone; and various dimethicone copolyols available either commercially or in the literature.

It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone. The higher concentration materials such as DOW CORNING® 2-5185 material is of particular interest.

In one particular embodiment 0.5–5 weight % (particularly 1.0–2.0%) of a 10% silicone copolyol such as dimethicone copolyol in cyclomethicone mixture may be used, wherein the amount of mixture added is selected so that the level of silicone copolyol in the cosmetic composition is in the range of 0.05–0.5% (particularly 0.1%) (for example, 1% of a 10% dimethicone copolyol in cyclomethicone mixture).

By volatile silicone material is meant a material that has a measurable vapor pressure at ambient temperature. For the volatile silicone portion, examples of volatile silicones (particularly silicones with a flash point of 100 degrees C or less at atmospheric pressure) include cyclomethicone (especially cyclopentasiloxane, also called "D5"), "hexamethyldisiloxane", and low viscosity dimethicone (for example, Dow Corning® 200 fluid having a viscosity of 0.5–5 centistokes). Such volatile silicones include conventional cyclic and linear volatile silicones Illustratively, and not by way of limitation, the volatile silicones are one or more members selected from the group consisting of cyclic polydimethylsiloxanes such as those represented by Formula III:

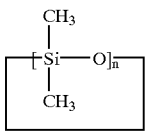

$$\begin{bmatrix} CH_3 \\ | \\ Si-O \\ | \\ CH_3 \end{bmatrix}_n \qquad \text{Formula III}$$

where n is an integer with a value of 3–7, particularly 5–6. For example, DC-245 fluid (or the DC-345 version) from Dow Corning Corporation (Midland, Mich.) is a type of cyclomethicone which can be used. These include a tetramer (or octylmethylcyclotetrasiloxane) and a pentamer (or decamethylcyclopentasiloxane). The volatile linear silicones can also be included in this group of volatile silicones and are one or more members selected from the group consisting of linear polydimethylsiloxanes such as those represented by Formula IV:

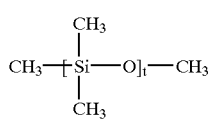

$$CH_3-\begin{matrix} CH_3 \\ | \\ Si-O \\ | \\ CH_3 \end{matrix}_t-CH_3 \qquad \text{Formula IV}$$

and t is selected to obtain a viscosity of 0.5–5 centistokes.

Examples of such volatile silicones include one or more members selected from the group consisting of D4, D5, and D6 cyclomethicones; and linear dimethicones having a viscosity in the range of 0.5–5 centistokes. Preferably the oil phase is a mixture of one or more of D4, D5 and D6 cyclomethicones (for example, a mixture of D5 and D6 cyclomethicones).

The viscosity of the final product should be in the range of 5–50,000 centipoise.

According to another aspect of the present invention, the aqueous phase of the clear cosmetic gel composition further optionally includes at least one polypropylene glycol. Illustratively, tripropylene glycol can be utilized as the polypropylene glycol. According to this aspect of the present invention, propylene glycol can be used in combination with the polypropylene glycols. Incorporation of the polypropylene glycol in the gel composition improves cosmetic properties, including a reduction of tack and a decrease in the whitening and in the residue after application of the composition. Moreover, compositions incorporating polypropylene glycol, particularly, tripropylene glycol, have improved mildness (that is, reduced skin irritation potential) relative to commercially available products.

Optionally one or more emollients may be included. Emollients are a known class of materials in this art, imparting a soothing effect to the skin. These are ingredients which help to maintain the soft, smooth, and pliable appearance of the skin. Emollients are also known to reduce whitening on the skin and/or improve aesthetics. Examples of chemical classes from which suitable emollients can be found include:

(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula VI:

Formula VI

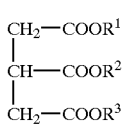

wherein each of $R^1$, $R^2$, and $R^3$ may be the same or different and each have a carbon chain length (saturated or unsaturated) of 7 to 25. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil;

(b) hydrocarbons which are a group of compounds containing only carbon and hydrogen. These are derived from petrochemicals. Their structures can vary widely and include aliphatic, alicyclic and aromatic compounds. Specific examples include paraffin, petrolatum, hydrogenated polyisobutene, and mineral oil.

(c) esters which chemically, are the covalent compounds formed between acids and alcohols. Esters can be formed from almost all acids (carboxylic and inorganic) and any alcohol. Esters here are derived from carboxylic acids and an alcohol. The general structure would be $R^4CO-OR^5$. The total number of carbons in $R^4$ and $R^5$ combined is in the range of 7–40 and the carbons chain can be saturated or unsaturated, straight chained or branched. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, dipropylene glycol dibenzoate, $C_{12-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fumarate, laureth-2 benzoate, propylene glycol isoceteth-3 acetate, propylene glycol ceteth-3 acetate, octyldodecyl myristate, cetyl ricinoleate, myristyl myristate.

(d) saturated and unsaturated fatty acids which are the carboxylic acids obtained by hydrolysis of animal or vegetable fats and oils. These have general structure $R^6COOH$ with the $R^6$ group having a carbon chain length in the range of 7 and 25, straight chain or branched. Specific examples include lauric, myristic, palmitic, stearic, oleic, linoleic and behenic acid.

(e) saturated and unsaturated fatty alcohols (including guerbet alcohols) with general structure $R^7COH$ where $R^7$ can be straight or branched and have 7 to 25 carbons. Specific examples include lauryl, myristyl, cetyl, isocetyl, stearyl, isostearyl, oleyl, ricinoleyl and erucyl alcohol;

(f) lanolin and its derivatives which are a complex esterified mixture of high molecular weight esters of (hydroxylated) fatty acids with aliphatic and alicyclic alcohols and sterols. General structures would include $R^8CH_2-(OCH_2CH_2)_nOH$ where $R^8$ represents the fatty groups derived from lanolin and n=5 to 75 or $R^9CO-(OCH_2CH_2)_nOH$ where $R^9CO-$ represents the fatty acids derived from lanolin and n=5 to 100. Specific examples include lanolin, lanolin oil, lanolin wax, lanolin alcohols, lanolin fatty acids, isopropyl lanolate, ethoxylated lanolin and acetylated lanolin alcohols.

(g) alkoxylated alcohols wherein the alcohol portion is selected from aliphatic alcohols having 2–18 and more particularly 4–18 carbons, and the alkylene oxide portion is selected from the group consisting of ethylene oxide, and propylene oxide having a number of alkylene oxide units from 2–53 and, more particularly, from 2–15. Examples include cetyl glyceryl ether; isostearyl glyceryl ether; isostearyl glyceryl pentaerythrityl ether; laureth-5 butyl ether; oleyl glyceryl ether; PEG-4 ditallow ether; polyglyceryl-3 cetyl ether; polyglyceryl-4 lauryl ether; PPG-9 diglyceryl ether; propylene glycol myristyl ether. More specific examples include PPG-14 butyl ether, PPG-53 butyl ether laureth-5 butyl ether and PEG-4 ditallow ether.

(h) ethers selected from the group consisting of dicaprylyl ether; dicetyl ether; dimethyl ether; distearyl ether; ethyl ether; isopropyl hydroxycetyl ether; methyl hexyl ether; polyvinyl methyl ether;

(i) silicones as the linear organo-substituted polysiloxanes which are polymers of silicon/oxygen with general structure:

(1) $(R^{10})_3SiO(Si\ (R^{11})_2O)_xSi(R^{12})_3$ where $R^{10}$, $R^{11}$ and $R^{12}$ can be the same or different and are each independently selected from the group consisting of phenyl and C1–C60 alkyl; or (2) $HO(R^{14})_2SiO(Si\ (R^{15})_2O)_xSi(R^{16})_2OH$, where $R^{14}$, $R^{15}$ and $R^{16}$ can be the same or different and are each independently selected from the group consisting of phenyl and C1–C60 alkyl; (with specific examples including dimethicone, dimethiconol behenate, $C_{30-45}$ alkyl methicone, stearoxytrimethylsilane, phenyl trimethicone and stearyl dimethicone).

(j) adipic acid blends selected from the group consisting of trimethyl pentanediol/adipic acid copolymer (LEXOREZ TL8 from Inolex, Philadelphia, Pa.); trimethyl pentanediol/adipic acid/isononanoic acid copolymer (LEXOREZ TC8); and adipic acid/diethylene glycol/glycerin crosspolymer (LEXOREZ 100);

(k) mixtures and blends of two or more of the foregoing.

A particular grouping of emollients is as follows in a total amount of 0–10 weight percent:

(i) fats and oils which are animal or plant based, saturated or unsaturated glyceryl esters of fatty acids, or triglycerides; synthetically prepared esters of glycerin and fatty acids; fats and oils represented by Formula VI:

Formula VI

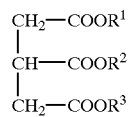

wherein each of $R^1$, $R^2$, and $R^3$ may be the same or different and have a carbon chain length (saturated or unsaturated) of 7 to 25;

(ii) hydrocarbons which are aliphatic, alicyclic or aromatic compounds and have 7–40 carbons;

(iii) esters of formula $R^4CO-OR^5$ wherein the number of carbons in $R^4$ and $R^5$ combined is in the range of 7–40 and can be saturated or unsaturated, straight chained or branched;

(iv) saturated and unsaturated fatty acids of formula $R^6COOH$ wherein $R^6$ is an alkyl group having a carbon chain length between 7 and 25, straight chain or branched;

(v) saturated and unsaturated fatty alcohols of formula $R^7COH$ where $R^7$ is an alkyl group having a carbon length of 7 to 25;

(vi) lanolin and its derivatives which are a complex esterified mixture of high molecular weight esters of (hydroxylated) fatty acids with aliphatic and alicyclic alcohols and sterols of formula $R^8CH_2$—$(OCH_2CH_2)_n$OH where $R^8$ is a fatty group derived from lanolin and n=5 to 75 or formula $R^9CO$—$(OCH_2CH_2)_nOH$ where $R^9CO$— is a fatty acid derivative derived from lanolin and n=5 to 100;

(vii) alkoxylated alcohols wherein the alcohol portion is selected from aliphatic alcohols having 2–18 carbons, and the alkylene oxide portion is selected from the group consisting of ethylene oxide, and propylene oxide having a number of alkylene oxide units from 2–53;

(viii) ethers selected from the group consisting of dicaprylyl ether; dicetyl ether; dimethyl ether; distearyl ether; ethyl ether; isopropyl hydroxycetyl ether; methyl hexyl ether; polyvinyl methyl ether;

(ix) silicones which are linear organo-substituted polysiloxanes that are polymers of silicon/oxygen with general structure selected from the group consisting of:
(1) $(R^{10})_3SiO(Si\ (R^{11})_2O)_xSi(R^{12})_3$ where $R^{10}$, $R^{11}$ and $R^{12}$ can be the same or different and are each independently selected from the group consisting of phenyl and C1–C60 alkyl; and
(2) $HO(R^{14})_2SiO(Si\ (R^{15})_2O)_xSi(R^{16})_2OH$, where $R^{14}$, $R^{15}$ and $R^{16}$ can be the same or different and are each independently selected from the group consisting of phenyl and C1–C60 alkyl;

(xi) adipic acid blends selected from the group consisting of trimethyl pentanediol/adipic acid copolymer; trimethyl pentanediol/adipic acid/isononanoic acid copolymer; and adipic acid/diethylene glycol/glycerin crosspolymer; and (xii) mixtures and blends of two or more of the foregoing.

Particular examples of suitable emollients include members of the group consisting of Octyloxyglyderin (SENSIVA SC50 from Schuilke Mayr, Norderstedt, Germany) (which can be used as an emollient as well as an antibacterial); Polysorbate 80 (TWEEN 80 from ICI Americas, Wilmington, Del.); Oleth-20; ethoxylated alcohols such as steareth-2, nonoxynol-2, PPG-4–Ceteth-1; ethoxylated carboxylic acids such as PEG-4 dilaurate, PEG-2 oleate; glyceryl esters such as PEG-2 castor oil, polyglyceryl-3 oleate, glyceryl stearate; sorbitan derivatives such as sorbitan oleate; PPG-3 myristyl ether (such as WITCONOL APM from Goldschmidt), a dimethiconol (such as Dow Coming® DC1501 dimethiconol), neopentyl glycol diheptanoate, PEG-8 laurate, isocetyl stearate, dimethicone copolyol laurate, Dow Coming 2501 cosmetic wax (dimethicone copolyol); isostearyl isostearate, isostearyl palmitate, isostearyl alcohol, PPG-5-ceteth-20, PPG-10-cetyl ether, triethyl hexanoin, ethyl hexyl isostearate, glyceryl oleate, isopropyl isostearate PPG-3 myristyl ether, hydrogenated polyisobutene, C12–15 alkyl benzoate and dimethicones having a viscosity in the range of 20–10,000 centistokes.

Even more particular examples include PPG-3 myristyl ether, hydrogenated polyisobutene, C12–15 alkyl benzoate and dimethicones having a viscosity in the range of 100–1000 centistokes.

The emollient or emollient mixture or blend thereof incorporated in compositions according to the present invention can, illustratively, be included in amounts of 0.5–10%, preferably 1–5%, more preferably 3–5%, by weight, of the total weight of the composition.

In one embodiment of the invention, the oil phase of the cosmetic gel composition according to the present invention includes a volatile silicone fluid and an emollient. Preferably, such emollient, which can be a silicone material (such as phenyl trimethicone), is the material of the oil phase having the high refractive index, and has a refractive index higher than that of the volatile silicone fluid and higher than that of the non-volatile silicone fluid (that is, this emollient is, desirably, a high refractive index emollient compatible with the silicone fluids of the oil phase).

The objectives of the present invention are also achieved through the method of forming the liquid cosmetic gel compositions described herein. In this method, an aqueous-based phase comprising water and the antiperspirant active is formed. Also formed is an oil-based phase containing at least a high refractive index material (a material having a refractive index in the range of 1.3950 to 1.55) and an alkoxylated, alkyl substituted siloxane surface active agent, and desirably other silicone fluids. The refractive index of the oil-based phase is determined, and, if necessary, adjusted to be in the range from about 1.4000 to about 1.4100, and the refractive index of the aqueous-based phase is determined and adjusted (if necessary) to differ from the refractive index of the oil-based phase by less than 0.0005. The aqueous-based phase is then mixed with the oil-based phase (for example, the aqueous-based phase is slowly added to the oil-based phase with turbulent agitation), and then additional additives, such as fragrance and color or other active ingredients, are added with mixing. The resulting emulsion is then passed through, for example, a colloid mill or other high shear emulsifier so as to provide a viscous gel, the gel then being transferred to a suitable applicator or container for use by the consumer. Desirably, according to the present invention the aqueous-based phase further includes polypropylene glycol, such as tripropylene glycol, providing advantages in the final product as discussed previously.

The compositions according to the present invention are used as conventional cosmetic gel compositions. For example, where the composition according to the present invention is a clear antiperspirant soft gel composition, packaged in a dispensing container having a top surface with slots or pores, the gel is extruded from the dispensing container through the slots or pores and applied to the skin (for example, in axillary regions of the human body) by rubbing the soft gel material extruded through the top surface of the container on the skin in the axillary region.

As a further aspect of the present invention, the dispensing container is a clear container, so as to exhibit the clarity of the composition of the present invention.

The composition has reduced tack, a cool sensation, and a silky feel and imparts much less or no white residue on dry down compared to commercially available products. Moreover, compositions of the present invention incorporating a polypropylene glycol component (especially tripropylene glycol) have improved mildness (have reduced skin irritation potential) as compared to commercially available products, and have improved cosmetic properties (including reduced tackiness) and reduced white residue upon application.

Throughout the present disclosure, the present invention is described primarily in connection with a clear liquid gel antiperspirant and/or deodorant composition.

Throughout the present specification, the antiperspirant active materials, when utilized in an antiperspirant effective amount in the composition, act to reduce body malodor by reducing production of perspiration; however, these antiperspirant active materials can also have a deodorant function, e.g., as an antimicrobial agent. The deodorant active materials do not substantially reduce the production of perspiration, but reduce malodor in other ways, e.g., as fragrances masking the malodor or reducing the malodor intensity, as odor absorbents, as antimicrobial agents, as agents chemically reacted with malodorous materials, etc.

Throughout the present specification, where compositions are described as including or comprising specific components or materials, it is contemplated by the inventors that the compositions of the present invention also consist essentially of, or consist of, the recited components or materials. Accordingly, throughout the present disclosure any described composition of the present invention can consist essentially of, or consist of, the recited components or materials.

A desired feature of the present invention is that a clear, or transparent, cosmetic gel composition (e.g., clear or transparent deodorant or antiperspirant gel composition) can be provided. The term clear or transparent (that is clarity), according to the present invention, is intended to connote its usual dictionary definition; thus, a clear, e.g., cosmetic gel composition of the present invention allows ready viewing of objects behind it. By contrast, a translucent composition allows light to pass through, but causes the light to be so scattered that it will be impossible to see clearly objects behind the translucent composition. Optical clarity of compositions of the present invention can be measured using a turbidmeter, and desirably is less than 50 NTU measured at room temperature (20°–25° C.).

An optically clear cosmetic (e.g., antiperspirant or deodorant) gel composition that is visually clear, and, like glass, allows for the viewing of the objects behind it, can be achieved. In particular, a composition having an optical clarity less than 50 NTU at room temperature (20°–25° C.), preferably having a turbidity measurement less than 30 NTU, more preferably less than 20 NTU, can be achieved.

Moreover, the clear cosmetic gel composition of the present invention, which is in the form of a macro-emulsion as contrasted to a micro-emulsion, does not need to contain wax or gelling agents such as soaps, cellulosic materials or alginates. Furthermore, the composition according to the present invention does not require polydimethylcyclosiloxane, although the present compositions may contain this material.

The gel emulsions according to the present invention are stable and optically clear, are cosmetically elegant, and are capable of being delivered from a suitable applicator package. They are easily applied to the skin and have a smooth, silky feel and a cool sensation, yet are fast drying and non-tacky. These compositions of the present invention may be prepared by a batch process, or a continuous or semi-continuous process, and the processes yield compositions which are stable, highly efficacious and possess excellent aesthetic qualities.

The amount of active component that can be used will vary with the particular active ingredient incorporate. As a general rule, an antiperspirant product should contain an active antiperspirant material in an amount anywhere from about 9% to about 25% by weight, of the total weight of the composition. The active antiperspirant material utilized in the compositions of the present invention can be pre-dissolved in water or in another solvent (for example, in propylene glycol), and may be buffered or unbuffered. Preferably, the antiperspirant materials are present in solution in a solvent.

Where a deodorant active material is utilized other than lower amounts of an antiperspirant active (which can be used in amounts in the range of 0.1–9.0 weight %), any deodorant active material, which can be dissolved in the oil phase, can be utilized in an amount sufficient to have a deodorant effect. Illustratively, the deodorant active material can be 2,4,4'-trichloro-2'-hydroxy diphenyl ether (triclosan), and/or benzethonium chloride. Where the deodorant ingredient is used in place of the antiperspirant active ingredient, a deodorant gel composition (rather than an antiperspirant gel composition) would be provided.

The aqueous phase includes at least water (refractive index of 1.3333) and 0–10 weight % of one or a combination of various other polar species. Other polar species include polyhydric alcohols and ethers thereof (for example, tripropylene glycol, diethylene glycol monoethyl ether). Illustratively, water can be included in the compositions in an amount in the range of 30% to 70% by weight, of the total weight of the composition (for example, 50–60%).

The oil phase according to the present invention is, desirably, a silicone oil phase, so as to provide a water-in-silicone oil emulsion. The total of oil phase and siloxane surface-active agent preferably makes up from about 10% to about 24% by weight, of the total weight of the composition. This surface-active agent is an emulsifier which, when properly mixed with the aqueous phase components, oil phase components and coupling agents, yields a water-in-oil emulsion. The oil phase is desirably a blend of liquids, but does not contain any significant amount of non-volatiles (that is, less than 5.0 weight % of any material having a flash point greater than 100 degrees C.)

The oil phase can include, illustratively, a volatile silicone fluid such as one or more of D4, D5 and D6 cyclomethicones, as well as phenyl dimethicone. Where the composition includes the volatile silicone, it is preferred that such volatile silicone be a polydimethylcyclosiloxane, present in an amount up to about 23.95% by weight, of the total weight of the composition, preferably from about 10% to about 20% by weight, of the total weight of the composition. Preferred polydimethylcyclosiloxanes are those named cyclomethicones, exemplified by the formula $((CH_3)_2SiO)_x$ where x is a number from about 4 to about 6. Preferred cyclosiloxanes are octamethylcyclotetrasiloxane (x=4), decamethylcyclopentasiloxane (x=5) and blends of tetramer and pentamer cyclomethicones. Commercial cyclosiloxanes which can be utilized as part of the composition of the present invention include, illustratively, Dow Corning 244 fluid, Dow Corning 245 fluid, Dow Corning 344 fluid and Dow Corning 345 fluid (from Dow Corning Corp.).

Preferably the oil phase is a mixture of volatile silicone fluids such as one or more of D4, D5 and D6 cyclomethicones, especially D5 and D6 cyclomethicones.

A particular example of an alkoxylated, alkyl substituted siloxane surface active agent is preferably, but not limited to, a dimethicone copolyol. An illustrative alkoxylated silicone-containing surfactant utilizable according to the present invention is cetyl dimethicone copolyol, referred to in U.S. Pat. No. 5,162,378 to Guthauser. Illustratively, the alkoxylated, alkyl substituted siloxane surface active agent is included in the composition in an amount of 0.05% to 0.5% by weight, of the total weight of the composition. Another example of a suitable surfactant is octyl dimethicone ethoxy glucoside (from Wacker-Belsil, Adrian, Mich.).

A specific cyclomethicone-dimethicone copolyol fluid which can be utilized to provide the alkoxylated silicone-containing surface-active agent is a mixture of cyclomethicone and dimethicone copolyol designated as DC 5225C from Dow Corning Corporation. This is a polyether substituted silicone of cyclomethicone and dimethicone copolyol (refractive index (RI)=1.3994) at about 20–25 degrees C. This DC 5225C, which is an emulsifying agent, is useful for preparing stable water-in-oil emulsions where a silicone makes up a large portion of the oil phase, and is a dispersion of a silicone surfactant (dimethicone copolyol) (10% by wt.) in cyclomethicone (Dow Coming 344 Fluid) (90% by weight).

The mixture of cyclomethicone and dimethicone copolyol fluid is present in the composition, illustratively, in an amount of from about 9% to about 24% by weight, of the total weight of the composition.

Various materials incorporated in the water-based phase and in the oil-based phase, and their refractive indices (as measured using the Bausch and Lomb Abbe 3L Refractometer) are set forth in the following:

Particular formulations of the products of the invention include the following:

- 0.5–5.0 weight % dimethicone copolyol/cyclomethicone (10%) (for example, Dow Coming 5225C);
- 10–20 weight % cyclomethicone (D4, D5, D6 or mixtures thereof);
- 0–5.0 weight % PPG-3 myristyl ether;
- 0–5.0 weight % of an additional emollient selected from the group consisting of straight or branched chain hydrocarbons and alkyl esters having 8–18 carbons (for example, C12–15 alkyl benzoate such as FINSOLV TN from Finetex, Elmwood Park, N.J.) and hydrogenated polyisobutene (for example Polyiso 250 from the Fanning Corp., Chicago, Ill.);
- 0–1.0 weight % sage oil (any type such as Clary or Dalmation);
- 0–5 weight % fragrance;
- 10–20 weight % antiperspirant active (for example, Al—Zr tetrachlorohydrex gly (such as Z-522, 30% from Summit Research Labs, Huguenot, N.Y. as described in U.S. Ser. No. 09/693,231 referenced above));
- 50–60 weight % water;
- 0–5 weight % of one or glycols selected from propylene glycol, dipropylene glycol and tripropylene glycol;

wherein the composition has a phase ratio in the range of 10:90–24:76 of oil to water and a viscosity in the range of 5–50,000 centipoise.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C unless otherwise indicated. The amounts of the components are in weight percents based on the standard described; if no other standard is described then the total weight of the composition is to be inferred. Various names of chemical components include those listed in the CTFA International Cosmetic Ingredient Dictionary (Cosmetics, Toiletry and Fragrance Association, Inc., 7$^{th}$ ed. 1997). Refractive Indices ("RI") are determined at a temperature in the range of 20–25 degrees C.

Examples 2/24: 5/28; and 6/29

For Examples 2/24; 5/28; and 6/29 the following procedure may be used with the types and amounts of ingredients listed in Table A. The sample sizes are about 400 grams. Silicone copolyol, cyclomethicone and fragrance are weighed and combined in a beaker. The mixture is stirred at 300–400 rpm using a Lightnin Mixer Model LI003. After the mixture becomes visually homogeneous, the active phase containing the antiperspirant active in water and the rest of the ingredients (tripropylene glycol and propylene glycol) are added. The entire mixture is mixed for 15 minutes. The mixture is then homogenized for 1–1.5 minutes at a reading of 40–60 on Powerstat Variable Transformer (Superior Electric Co., Bristol, Conn.) using a homogenizer from Greerco Corp. (Hudson, N.H.).

TABLE A

| Ingredients (weight %) | Ex. 2/24 | Ex. 5/28 | Ex. 6/29 |
| --- | --- | --- | --- |
| Cyclomethicone | 17.5 | 18 | 22 |
| Dimethicone copolyol/cyclomethicone (DOW Corning 5225C, (10%) | 1.5 | 1 | 1 |
| Fragrance | 1 | 1 | 1 |
| Active* | 64.5 | 66 | 66 |
| Tripropylene glycol | 5 | — | — |
| Water | 10.5 | 11 | 10 |
| Propylene glycol | — | 3 | — |
| Total | 100 | 100 | 100 |

*Al—Zr tetrachlorohydrex glycine complex (Z522, 30% in water from Summit Research Labs which is a salt of the type described in Methods A and B above.

Examples 7/9; 8/13; 9/18; 10/26; 11/27; 12/31; 13/33; 14/36; 15/49; 16/53; 17/60; SE-1 and SE-2

For Examples 7/9; 8/13; 9/18; 10/26; 11/27; 12/31; 13/33; 14/36; 15/49; 16/53; 17/60; SE-1 and SE-2 the following procedure may be used with the types and amounts of ingredients listed in Tables B, C and D. The sample sizes are about 400 grams. The ingredients for the oil phase (silicone copolyol, cyclomethicone, PPG-3 myristyl ether) are weighed and combined in a beaker. The mixture is stirred at 300–400 rpm for 5 minutes using a Lightnin Mixer Model L 1003. After the mixture becomes visually homogeneous, the active phase containing the antiperspirant active in water and the rest of the ingredients (tripropylene glycol and propylene glycol) are added. The entire mixture is mixed for 15 minutes. The mixture is then homogenized for 1–1.5 minutes at a reading of 40–60 on Powerstat Variable Transformer (Superior Electric Co., Bristol, Conn.) using a homogenizer from Greerco Corp. (Hudson, N.H.).

TABLE B

| Ingredient (weight %) | Ex. 7/9* | Ex. 8/13 | Ex. 9/18 | Ex. 10/26 | Ex. 11/27 |
| --- | --- | --- | --- | --- | --- |
| Dimethicone copolyol/cyclomethicone (Dow Corning 2-5185C, 50%) | 1.0 | — | — | — | — |
| Dimethicone copolyol/cyclomethicone (Dow Corning 5225C, 10%) | — | 1.0 | 3.0 | 1.0 | 1.5 |
| Cyclomethicone | 15.0 | 18.0 | 16.0 | 18.0 | 17.5 |
| PPG-3 myristyl ether | 1.0 | — | — | — | — |
| Fragrance | 1.0 | 1.0 | 1.0 | 1.0 | 1.0 |
| Active (same as in TABLE A) | 63.5 | 64.0 | 64.5 | 64.5 | 66.0 |
| Water | 10.5 | 11.0 | 10.5 | 10.5 | 11.0 |
| Propylene glycol | 8.0 | — | — | — | 3.0 |
| Tripropylene glycol | — | 5.0 | 5.0 | 5.0 | — |
| Total | 100.0 | 100.0 | 100.0 | 100.0 | 100.0 |

TABLE B-continued

| Ingredient (weight %) | Ex. 7/9* | Ex. 8/13 | Ex. 9/18 | Ex. 10/26 | Ex. 11/27 |
|---|---|---|---|---|---|

*A comparative example made with 27.0% cyclomethicone instead of 15.0%; 6.5% water instead of 10.5%; and 0% propylene glycol instead of 8.0% had a phase ratio of 25:75 (outside the claimed range) and was not stable (emulsion fell apart and separated.)

TABLE C

| Ingredient (weight %) | Ex. 12/31 | Ex. 13/33* | Ex. 14/36 | Ex. 15/49 | Ex. 16/53 |
|---|---|---|---|---|---|
| Dimethicone copolyol/ Cyclomethicone (Dow Corning 2-5185C, 50%) | — | — | — | — | — |
| Dimethicone copolyol/ cyclomethicone (Dow Corning 5225C, 10%) | 1.0 | 11.5 | 1.0 | 1.5 | 1.5 |
| Silicone elastomer (Dow Corning DC 9040) | | | | | |
| Cyclomethicone | 17.0 | 10.5 | 18.0 | 17.5 | 17.5 |
| PPG-3 myristyl ether | — | — | — | — | — |
| Sage oil | 1.0 | 1.0 | — | — | — |
| Fragrance | 1.0 | 1.0 | 1.0 | 0.985 | 0.985 |
| Active (same as in TABLE A) | 66.0 | 66.0 | 66.0 | 33.3 | 66 |
| Water | 9.0 | 8.0 | 11.0 | 26.7 | 11 |
| Propylene glycol | 5.0 | 2.0 | 3.0 | 20 | 3 |
| BHT | — | — | — | 0.015 | 0.015 |
| Total | 100.0 | 100.0 | 100.0 | 100.0 | 100.0 |

*A comparative example made with 12.5% Dow Corning 5225C instead of 11.5% and 7.0% water instead of 8.0% had a phase ratio of 25:75 (outside the claimed range) and was not stable (emulsion fell apart and separated.)

TABLE D

| Ingredient (weight %) | Ex. 17/60 | Ex. SE-1 | Ex. SE-2 |
|---|---|---|---|
| Dimethicone copolyol/ cyclomethicone (Dow Corning 2-5185C, 50%) | — | 0.5 | 0.5 |
| Dimethicone copolyol/ cyclomethicone (Dow Corning 5225C, 10%) | 1.5 | — | — |
| Silicone elastomer (Dow Corning DC 9040) | — | 15 | 15 |
| Cyclomethicone | 17.5 | 13.5 | 13.5 |
| PPG-3 myristyl ether | — | 2.0 | 2.0 |
| Fragrance | 1.0 | 1.0 | 1.0 |
| Active (same as in TABLE A) | 16.7 | 32.4 | 16.2 |
| Water | 60.3 | 35.6 | 51.8 |
| Propylene glycol | 3.0 | — | — |
| Total | 100.0 | 100.0 | 100. |

Example TFR #1

Thin Film Release Evaluated by Conductivity

The magnitude of an antiperspirant effect is dependent on the dose of active released from the formulation while present in the axilla. In order to evaluate the amount of active released from antiperspirant formulas, a conductometry method was developed to measure antiperspirant salt released from a product film over time. Since the primary ionic species present in the formulations being tested were antiperspirant salts, conductometry measured the release of the salts directly. In addition, a fixed geometry probe, which allowed measurement of absolute solution conductance, may be used to calculate the actual mass of antiperspirant salt released. The fixed geometry probe maintains a total surface area of the formulations exposed to water constant at 2.85 cm$^2$, with a film volume of 28.5 microliters ("$\mu l$") Experiments are conducted using simulated underarm conditions of approximately 33 degrees C and 91% relative humidity ("RH"). Thin films of antiperspirant product, 100 microns ("$\mu m$") thick and similar in mean thickness to product films applied in the axilla during actual use, are spread onto Plexiglas® plates. The films are then equilibrated at the underarm conditions for two hours. A two-hour equilibration period facilitates the redistribution of volatile components such as cyclomethicone and water in the antiperspirant film, and is hypothesized to mimic some of the changes occurring with use in the axilla. After two hours equilibration, 0.45 ml of 18 Mega Ohm (M$\Omega$) resistance water is added to the well of each of four wells in the fixed geometry probe, and conductance data is collected for at least one hour from each well. The conductance data is then converted to micrograms ("$\mu g$") of Summit Z522/cm$^2$ of exposed film surface area using calibration charts developed for the Summit Z522 active.

The compositions of this invention will give values of greater than about 300 micrograms/cm$^2$/hour at a loading of 5 weight % active (exclusive of glycine and water of hydration content) as evaluated with the test described herein. Specific values were obtained for Examples 15/49, 16/53 and 17/60 as listed in Table E. Conductometry experiments with the simulated underarm conditions show that the liquid gel formulae as described in Examples 15/49, 16/53 and 17/60 ("Liquid Gel LG49, LG53 and LG60", respectively) is an efficient base for delivery and release of antiperspirant active. Note that the test results for the elastomer gel samples (Ex.SE-1 and SE-2) are significantly lower than the Liquid Gel LG49 and LG 17/60 (10% active and 5% active respectively, anhydrous Summit Z522). Also, by comparison, the release of active from a commercially available (and higher viscosity) antiperspirant gel, Speed Stick Gel Antiperspirant ("SSAP Gel"), is significantly lower, being only about 151 $\mu g$/cm$^2$/hour (or 58 minutes which is approximately an hour).

TABLE E

Test Data

| Formulation | Wt % Active[1,2] | $\mu g$/cm$^2$ Active Released in 58.3 min |
|---|---|---|
| Liquid Gel LG53 (Example 16/53) | 19.6[1] | 1687 |
| Liquid Gel LG49 (Example 15/49) | 10.0[1] | 957 |
| Liquid Gel LG60 (Example 17/60) | 5.0 | 366 |
| Silicone Elastomer Gel (Example SE-1) | 10.0[1] | 712 |
| Silicone Elastomer Gel (Example SE-2) | 5.0 | 179 |
| Speed Stick AP Gel | 18.06 | 151 |

[1] = Active used is Summit Z522, having a low metal to chloride ratio within the limits claimed.
[2] = The active is anhydrous except for waters of hydration. The amount of active listed in calculated without including glycine or waters of hydration.

What is claimed is:

1. A clear, elastomer-free, gel composition comprising:
   (a) 0.1–25 weight % of an antiperspirant active having a low metal to chloride ratio in the range of 0.9–1.3;
   (b) 9–23.95 weight % of one or more volatile silicones having a flash point of 100 degrees C or less;
   (c) 0.05–0.5 weight % of a silicone surfactant having an HLB value (hydrophilic lipophilic balance)$\leq 8$;

(d) 30–70 weight % water;
(e) 0–50 weight % of a water soluble organic solvent selected from the group consisting of ethanol, glycerol formal, propylene glycol, dipropylene glycol, and tripropylene glycol; and
(f) 0–10 weight % of an emollient;
wherein the composition is a liquid gel having a viscosity in the range of 5–50,000 centipoise and a ratio of oil phase to water phase in the range of 10:90 to 24:76.

2. A composition according to claim 1 which has a refractive index before addition of fragrance in the range of 1.3950–1.4150.

3. A clear antiperspirant and/or deodorant liquid gel composition as claimed in claim 1 wherein the metal to chloride ratio for the antiperspirant active is in the range of 0.9–1.05:1.

4. A composition according to claim 1 comprising 5–20 weight % of the antiperspirant active.

5. A composition according to claim 1 comprising 9–20 weight % of the volatile silicone.

6. A composition according to claim 1 comprising 0.1–0.2% of the silicone surfactant.

7. A composition according to claim 1 wherein the emollient comprises a member selected from the group consisting of:
(a) fats and oils which are the saturated or unsaturated glyceryl esters of fatty acids, or triglycerides and having a general structure represented by Formula VI:

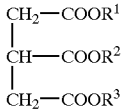

Formula VI wherein each of $R^1$, $R^2$, and $R^3$ may be the same or different and each have a carbon chain length of 7 to 25;
(b) hydrocarbons including aliphatic, alicyclic and aromatic compounds having 7–40 carbons;
(c) esters having a general structure of $R^4CO—OR^5$ wherein the total number of carbons in $R^4$ and $R^5$ together is in the range of 7 to 40 and can be saturated or unsaturated, straight chained or branched;
(d) saturated and unsaturated fatty acids having a general structure $R^6COOH$ wherein the $R^6$ group has a carbon chain length in the range of 7 to 25 and may be straight chain or branched;
(e) saturated and unsaturated fatty alcohols having a general structure $R^7COH$ wherein $R^7$ group has a carbon chain length in the range of 7 to 25 and may be straight chain or branched;
(f) lanolin and derivatives of lanolin having a general structure of $R^8CH_2—(OCH_2CH_2)_nOH$ where $R^8$ represents the fatty groups derived from lanolin and n=5 to 75 or $R^9CO—(OCH_2CH_2)_nOH$ where $R^9CO$— represents the fatty acids derived from lanolin and n=5 to 100;
(g) alkoxylated alcohols wherein the alcohol portion is selected from aliphatic alcohols having 2–18 carbons, and the alkylene oxide portion is selected from the group consisting of ethylene oxide, and propylene oxide having a number of alkylene oxide units from 2–53;
(h) ethers selected from the group consisting of dicaprylyl ether; dicetyl ether; dimethyl ether; distearyl ether; ethyl ether; isopropyl hydroxycetyl ether; methyl hexyl ether; and polyvinyl methyl ether;
(i) silicones as linear organo-substituted polysiloxanes which are polymers of silicon/oxygen with a general structure:
(1) $(R^{10})_3SiO(Si(R^{11})_2O)_xSi(R^{12})_3$ where $R^{10}$, $R^{11}$ and $R^{12}$ can be the same or different and are each independently selected from the group consisting of phenyl and C1–C60 alkyl; or
(2) $HO(R^{14})_2SiO(Si(R^{15})_2O)_xSi(R^{16})_2OH$, where $R^{14}$, $R^{15}$ and $R^{16}$ can be the same or different and are each independently selected from the group consisting of phenyl and C1–C60 alkyl;
(j) adipic acid blends selected from the group consisting of trimethyl pentanediol/adipic acid copolymer; trimethyl pentanediol/adipic acid/isononanoic acid copolymer; and adipic acid/diethylene glycol/glycerin crosspolymer;
(k) mixtures and blends of two or more of the foregoing.

8. A composition according to claim 7 wherein the emollient is selected from the group consisting of hydrogenated polyisobutene, C12–15 alkyl benzoate, and PPG-3 myristyl ether.

9. A composition as claimed in claim 1 comprising 9–20 weight % of the volatile silicone.

10. A composition as claimed in claim 1 wherein the silicone surfactant is a silicone polyglucoside.

11. A composition as claimed in claim 1 wherein the silicone surfactant is a silicone copolyol selected from Formulae I and II wherein:
(a) Formula I is:

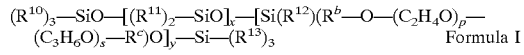

Formula I wherein each of $R^{10}$, $R^{11}$, $R^{12}$ and $R^{13}$ may be the same or different and each is selected from the group consisting of C1–C6 alkyl; $R^b$ is the radical —$C_mH_{2m}$—; $R^c$ is a terminating radical which can be hydrogen, an alkyl group of one to six carbon atoms, an ester group such as acyl, or an aryl group such as phenyl; m has a value of two to eight; p and s have values such that oxyalkylene segment —$(C_2H_4O)_p$—$(C_3H_6O)_s$— has a molecular weight in the range of 200 to 5,000; the oxyalkylene segment preferably has fifty to one hundred mole percent of oxyethylene units —$(C_2H_4O)_p$— and one to fifty mole percent of oxypropylene units —$(C_3H_6O)_s$—; x has a value of 8 to 400; and y has a value of 2 to 40
(b) Formula II is:

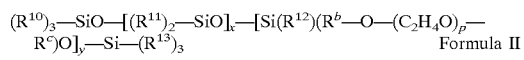

Formula II wherein p has a value of 6 to 16; x has a value of 6 to 100; and y has a value of 1 to 20 and the other moieties have the same definition as defined in Formula I; and
(c) alternate embodiments of both Formulae I and II wherein the linking group $R^b$, the oxyalkylene segments, and the terminating radical $R^c$ occupy positions bonded to the ends of the siloxane chain, rather than being bonded to a silicon atom in the siloxane chain.

12. A composition as claimed in claim 1 comprising 5–20 weight % of the antiperspirant active.

13. A composition as claimed in claim 7 wherein the emollient is selected from the group consisting of octyloxyglyderin; Polysorbate 80; Oleth-20; Steareth-2; nonoxynol-2; PPG-4-Ceteth-1; s PEG-4 dilaurate; PEG-2 oleate; PEG-2 castor oil; polyglyceryl-3 oleate; glyceryl stearate; sorbitan oleate; PPG-3 myristyl ether; a dimethiconol; neopentyl glycol diheptanoate; PEG-8 laurate; isocetyl stearate; dimethicone copolyol laurate; a cosmetic wax which is a dimethicone copolyol; isostearyl isostearate; isostearyl palmitate; isostearyl alcohol; PPG-5-ceteth-20; PPG-10-cetyl ether; triethyl hexanoin; ethyl hexyl isostearate; glyceryl oleate; isopropyl isostearate PPG-3 myristyl ether; hydrogenated polyisobutene; C12–15 alkyl benzoate; and dimethicones having a viscosity in the range of 20–10,000 centistokes.

14. A composition as claimed in claim 7 wherein the emollient is selected from the group consisting of PPG-3 myristyl ether, hydrogenated polyisobutene, C12–15 alkyl benzoate and dimethicones having a viscosity in the range of 20–10,000 centistokes.

15. A clear antiperspirant and/or deodorant liquid gel composition as claimed in either claim 1 or claim 7 comprising 0.5–10 weight % of emollient.

16. A composition as claimed in claim 1 which is free of waxes, soap gelling agents, cellulosics and alginates.

17. A composition as claimed in any one of claims 1–16 which has a clarity of less than 50 NTU at a temperature of 20–25 degrees C.

18. A composition as claimed in claim 1 additionally comprising a fragrance.

19. A composition as claimed in claim 7 comprising 10–20 weight % of a cyclomethicone; 30–70 weight % water; 10–20 weight % antiperspirant active; 0.05–0.5 weight % silicone copolyol; 0–5.0 weight % of an emollient selected from the group consisting of PPG-3 myristyl ether; polyisobutene, and C12–15 alkyl benzoate; 0–1.0 weight % sage oil; 0–5 weight % of a glycol selected from the group consisting of propylene glycol, dipropylene glycol, tripropylene glycol and mixtures thereof; and 0–5 weight % fragrance; wherein the composition has a phase ratio in the range of 10:90–24:76 of oil to water.

* * * * *